United States Patent
Kadobayashi et al.

(10) Patent No.: US 10,813,848 B2
(45) Date of Patent: *Oct. 27, 2020

(54) DENTAL PRIMER CONTAINING ACID ANHYDRIDE

(71) Applicant: SHOFU INC., Kyoto (JP)

(72) Inventors: Yusei Kadobayashi, Kyoto (JP); Masako Shigezawa, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/728,789

(22) Filed: Oct. 10, 2017

(65) Prior Publication Data

US 2018/0280254 A1 Oct. 4, 2018

(30) Foreign Application Priority Data

Mar. 31, 2017 (JP) ................................ 2017-071943

(51) Int. Cl.
*A61K 6/00* (2006.01)
*A61K 6/40* (2020.01)
*A61K 6/30* (2020.01)
*A61K 6/60* (2020.01)

(52) U.S. Cl.
CPC .................. *A61K 6/40* (2020.01); *A61K 6/30* (2020.01); *A61K 6/60* (2020.01)

(58) Field of Classification Search
CPC ................................................. A61K 6/0029
See application file for complete search history.

(56) References Cited

U.S. PATENT DOCUMENTS

| | | | |
|---|---|---|---|
| 4,952,613 A | 8/1990 | Hosoda | |
| 6,770,265 B2 | 8/2004 | Ishihara et al. | |
| 2009/0076182 A1* | 3/2009 | Tanaka | A61K 6/0023 522/48 |
| 2009/0299006 A1* | 12/2009 | Shinno | A61K 6/0023 524/807 |
| 2010/0056664 A1* | 3/2010 | Ohtsuka | A61K 6/30 523/116 |
| 2010/0069524 A1* | 3/2010 | Tanaka | A61K 6/0023 522/171 |
| 2011/0112209 A1* | 5/2011 | Tanaka | A61K 6/0023 522/171 |
| 2012/0070794 A1 | 3/2012 | Craig et al. | |

FOREIGN PATENT DOCUMENTS

| | | |
|---|---|---|
| EP | 2 036 532 | 3/2009 |
| JP | 63-51308 | 3/1988 |
| JP | 2003-230574 | 8/2003 |
| JP | 2014-055115 | 3/2014 |
| JP | 2015-168672 | 9/2015 |

OTHER PUBLICATIONS

English machine translation of Aoki et al. (JP 2003-230574) (Year: 2003).*
Japanese Office Action, dated May 17, 2017 in corresponding Japanese Patent Application No. 2017-071943, with English language translation.
Kurata et al., "Synthesis of New Silane Coupling Agents with a Trimellitic Anhydride Group and Application as Primers for Ceramics and Alloys", Dental Materials Journal, vol. 26, No. 6: pp. 800-804 (2007).
Extended European Search Report, dated Jul. 3, 2018 in corresponding European Patent Application No. 17195701.2.
Demir et al., "Effect of maleic anhydride pretreatment on tensile bond strength of a silicone soft liner to a denture base polymer", The Journal of Adhesive Dentistry, vol. 13, No. 5: pp. 481-487 (2011).
Official Communication for Third Party Observation dated May 20, 2019, in the corresponding EP Patent application No. 17195701.2.
Material safety data sheet, Issue 1, Mar. 9, 2007, pp. 1-2.

* cited by examiner

*Primary Examiner* — Michael F Pepitone
(74) *Attorney, Agent, or Firm* — Wenderoth, Lind & Ponack, L.L.P.

(57) ABSTRACT

The present invention provides the dental primer for modifying surface of a dental restoration, comprising: an organic solvent, a silane coupling agent and an acid anhydride.

8 Claims, No Drawings

DENTAL PRIMER CONTAINING ACID ANHYDRIDE

CROSS-REFERENCE TO RELATED APPLICATIONS

This application is based on and claims the benefit of priority from Japanese Patent Application Serial No. 2017-071943 (filed on Mar. 31, 2017), the contents of which are hereby incorporated by reference in their entirety.

TECHNICAL FIELD

The present invention relates to a dental primer for modifying a surface of a dental restoration.

BACKGROUND

In recent years, a dental crown restoration technique has been frequently used. In this technique, a dental restoration which is prepared by cutting and machining an inorganic sintered body by using CAD/CAM technique is mounted in an oral cavity.

An inorganic sintered body is supplied in the form of moldings such as a block and a disk. And a dental restoration such as a crown, an inlay and an onlay is prepared by cutting and machining the moldings by using CAD/CAM. The cut dental restoration is adhered to a missing tooth in an oral cavity to recover the function of an oral cavity.

In addition, when the dental restoration which restores in an oral cavity is damaged, re-restoration by a newly prepared dental restoration or repair with composites using adhesive materials on a fracture surface of tooth may be performed.

In this repair, it is required to bond composite resin to a fracture surface of the dental restoration. Therefore, a dental primer which reforms a fracture surface of the dental restoration has been required.

Japanese Unexamined Patent Application Publication No. 2015-168672 and Japanese Unexamined Patent Application Publication No. 2014-55115 disclose a dental primer using a phosphoric acid-based monomer. However, a shelf life of this dental primer is short. Further, there has been a problem with the adhesive durability in a dental restoration which is reformed with such a conventional dental primer, and it has been difficult to endure the long-term adhesion.

SUMMARY OF THE INVENTION

Problems to be Solved by the Invention

Conventionally, the dental restoration prepared by cutting and machining an inorganic sintered body is bonded to a repair site in an oral cavity by using cement and/or adhesive materials after reforming the surface with a dental primer containing a silane coupling agent. However, in order to activate a silane coupling agent and to efficiently reform the surface of the dental restoration, in the primer containing the silane coupling agent, it has been required to mix with an acid water solution before use. The reason is that because a silane coupling agent cannot exist at a stable condition under the coexistence with the acid component, preservation stability and shelf life stability worsen, and, as a result, the adhesive ability of the dental restoration decreases. Therefore, it has been necessary that a silane coupling agent and an acid component are contained in separate packing forms respectively. In addition, the dental primer containing a silane coupling agent has a problem with preservation stability and shelf life stability such as the decreasing of the adhesive ability of the dental restoration over time, even in the condition that acidic component is not contained. Therefore, a dental primer having excellent preservation stability and shelf life stability, having excellent operability because the mixing with an acid ingredient use is unnecessary before the use, and being able to modify the surface of the dental restoration is required.

The present invention provides a dental primer for modifying a surface of a dental restoration, comprising an organic solvent, a silane coupling agent and an acid anhydride.

It is preferable that the dental primer of the present invention comprises 80 to 99% by weight of the organic solvent, 0.1 to 15% by weight of the silane coupling agent, and 0.1 to 5% by weight of the acid anhydride. Further, it is preferable that the dental primer of the present invention comprises 90 to 98% by weight of the organic solvent, 1 to 8% by weight of the silane coupling agent, and 0.1 to 2% by weight of the acid anhydride. In addition, it is preferable that the dental primer of the present invention comprises no water. Furthermore, it is preferable that the dental primer of the present invention comprises no strongly acidic compound. In the present invention, the term "strongly acidic compound" means an acidic compound having pH of less than 2. In the present invention, the term "weakly acidic compound" means an acidic compound having pH of 2 or more.

Further, it is preferable that the acid anhydride is an anhydride of a carboxylic acid, a sulfonic acid, a nitric acid and/or a phosphoric acid. In addition, it is preferable that the dental primer of the present invention comprises no polymerizable monomer having an acryloyl group and/or a methacryloyl group.

The present invention provides a set comprising the dental primer of the present invention and an adhesive material. In this case, it is preferable that the adhesive material comprises a polymerizable monomer and a polymerization catalyst. It is preferable that the adhesive material comprises a filler. When the adhesive material comprises a filler, it is generally called as resin cement.

The present invention provides a set comprising the dental primer of the present invention and a dental restoration. In this case, it is preferable that the dental restoration comprises a polymerizable monomer, a polymerization catalyst and a filler.

It is preferable that the set of the present invention comprises a polymerizable monomer, a polymerization catalyst and a filler only in the adhesive material or the dental restoration.

It is preferable that the dental primer of the present invention comprises no polymerizable monomer. Further, it is preferable that the dental primer of the present invention comprises no polymerization catalyst. The reason is that it is important in the dental primer of the present invention to modify the surface of an adhesive body and an adherend.

It is preferable that the dental primer of the present invention is a dental primer for modifying a surface of a dental restoration, is prepared by cutting and machining an inorganic sintered body and consists of an organic solvent, a silane coupling agent and an acid anhydride.

The dental primer of the present invention may reform the surface of the dental restoration and the dental restoration which is reformed with the dental primer of the present invention may adhere to a composite resin via an adhesive material containing a polymerizable monomer. In particular, the dental restoration modified with the dental primer of the present invention is excellent in adhesive durability, and can maintain the adhesion for a long term under the oral cavity environment. Furthermore, the dental primer of the present invention may extend a shelf life.

In recent years, CAD/CAM technique is introduced in the dental field, and a dental restoration is prepared by cutting and machining a block and a disk which are an inorganic sintered body, and a restoration technique in which this dental restoration is applied into an oral cavity has been used in a clinical. A surface of the dental restoration cannot be reformed enough by the dental primer containing a silane coupling agent and having been used conventionally. Therefore, sufficient adhesive property of the dental restoration is not obtained even if combined with dental adhesive resin cement. However, adhesive property and adhesive durability of the dental restoration are increased by using the dental primer of the present invention.

Specifically, it becomes possible to adhere in excellent adhesive durability by performing adhesion work in accordance with a technique type of an adhesive resin cement after application of the dental primer of the present invention to an inner surface of the dental restoration which is prepared by cutting and machining an inorganic sintered body.

Further, on the cutting surface of the dental restoration consisting of the cured composite resin, which is also the dental restoration, an inorganic filler in the composite resin is exposed to the surface. Therefore, the same effect as that of the dental restoration of an inorganic sintered body may be obtained by the same handling as that of the inorganic sintered body. Specifically, it becomes possible to adhere excellent in adhesive durability by the work of repairing in accordance with technique types of an adhesive material and a composite resin after application of the dental primer of the present invention to a cutting surface of the composite resin.

DETAILED DESCRIPTION OF THE PREFERRED EMBODIMENTS

The dental primer of the present invention is a dental primer for modifying a surface of a dental restoration which is prepared by cutting and machining an inorganic sintered body such as a block and a disk by using CAD/CAM technique. The materials of the inorganic sintered body are not limited particularly, but specific examples of the materials of the inorganic sintered body include a composition containing silica, alumina, or zirconia as a main component. In addition, the dental restoration prepared by cutting and machining an inorganic sintered body may include pigment.

The dental primer of the present invention may be used for a composite resin in which an inorganic filler is exposed to the adhesive surface.

The dental primer of the present invention may be used for a dental restoration which is prepared by building up. This dental restoration may be prepared by building up and sintering an inorganic filler, and is generally called as porcelain.

As an organic solvent used for the dental primer of the present invention, for example, methanol, ethanol, n-propanol, isopropanol and anhydride thereof, and acetone and methyl ethyl ketone can be utilized. Methanol, ethanol, propanol, acetone and anhydride thereof are preferable, and Anhydrous ethanol and acetone are most preferable. The content of the organic solvent is preferably 80 to 90% by weight, and more preferably 90 to 98% by weight.

As the silane coupling agent used for the dental primer of the present invention, there can be preferably used, not particularly limited, methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris(β-methoxyethoxy)silane, γ-methacryloyloxypropyl trimethoxysilane, γ-methacryloyloxypropyl tris(β-methoxyethoxy/silane, γ-chloropropyl trimethoxysilane, γ-chloropropylmethyl dimethoxysilane, γ-glycidoxypropyl trimethoxysilane, γ-glycidoxypropylmethyldiethoxysilane, β-(3,4-epoxycyclohexyl)ethyltrimethoxysilane, N-phenyl-γ-aminopropyltrimethoxysilane and hexamethyldisilazane. Particularly preferably, methyltrichlorosilane, dimethyldichlorosilane, γ-methacryloyloxypropyltrimethoxysilane and hexamethyldisilazane are used. The content of silane coupling agent is preferably 0.1 to 15% by weight, and more preferably 1 to 8% by weight.

As the silane coupling agent used for the dental primer of the present invention, there can be preferably used, not particularly limited, methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris(β-methoxyethoxy)silane, γ-methacryloyloxypropyl trimethoxysilane, γ-methacryloyloxypropyl tris(β-methoxyethoxy)silane, γ-chloropropyl trimethoxysilane, γ-chloropropylmethyl dimethoxysilane, γ-glycidoxypropyl trimethoxysilane, γ-glycidoxypropylmethyldiethoxysilane, β-(3,4-epoxycyclohexyl)ethyltrimethoxysilane, N-phenyl-γ-aminopropyltrimethoxysilane and hexamethyldisilazane. Particularly preferably, methyltrichlorosilane, dimethyldichlorosilane, γ-methacryloyloxypropyltrimethoxysilane and hexamethyldisilazane are used. The content of silane coupling agent is preferably 0.1 to 15% by weight, and more preferably 1 to 8% by weight.

As the acid anhydride used for the dental primer of the present invention, not only the acid anhydride of the organic acid such as carboxylic acid but also the acid anhydride of the inorganic acid such as a sulfuric acid, a nitric acid and a phosphoric acid. As the specific examples of the acid anhydride of the inorganic acid, disulfuric acid (pyrosulfuric acid) as an anhydride of the sulfuric acid, trifluoromethanesulfonic acid anhydride as an anhydride of sulfonic acid, dinitrogen pentoxide as a nitrate anhydride, pyrophosphoric acid (diphosphoric acid) and diphosphorus (tetraphosphorus decaoxide) pentoxide as an anhydride of phosphoric acid, and, diphosphorus trioxide as an anhydride of the phosphorous may be used.

Preferable acid anhydride is an acid anhydride having pH of 2 or more, and is a carboxylic acid based-compound, and more preferable acid anhydride consists of a carboxylic acid based-compound. As the carboxylic acid based-compound, tartaric acid, malic acid, citric acid, maleic acid, itaconic acid and aconitic acid are preferable. In particular, citric acid, maleic acid, itaconic acid and anhydride thereof are more preferable. The content of the acid anhydride is preferably 0.1 to 5% by weight, and more preferably 0.1 to 2% by weight. It is preferable that the acid anhydride contains an anhydride of a carboxylic acid, a sulfonic acid, a nitric acid and/or a phosphoric acid.

The dental primer of the present invention may be compounded with an antioxidant such as hydroquinone, hydroquinone monomethyl ether and butylated hydroxytoluene appropriately. In addition, the dental primer of the present invention may be used in gel state by compounding a viscosity control agent such as colloidal silica, glycerin and polyethylene glycol. In addition, it is preferable that the dental primer of the present invention comprises no water. It is preferable that the dental primer of the present invention comprises no polymerizable monomer having an acryloyl group and/or a methacryloyl group. It is more preferable that the dental primer of the present invention comprises no polymerizable monomer.

The adhesive material which is used in the set of the present invention with the dental primer of the present invention preferably comprise a polymerizable monomer and a polymerization catalyst. The resin cement which is used in the set of the present invention with the dental primer of the present invention preferably comprise a polymerizable monomer, a polymerization catalyst and a filler. The composite resin used in the set comprising the dental primer of the present invention and the adhesive material or the resincement comprises a polymerizable monomer, a polymerization catalyst and a filler.

The polymerizable monomer is not limited in particular as long as it is a polymerizable monomer having a polymerizable group. Specifically, known monofunctional and/or multifunctional polymerizable monomer(s) commonly used for a dental material can be used.

Preferable polymerizable monomers include polymerizable monomers having an acryloyl and/or methacryloyl group. Next, the names of specific polymerizable monomer are described.

Examples of polymerizable monomers having no acidic group include:

monofunctional monomers (non-crosslinkable monomers): such as (meth)acrylic acid esters such as methyl (meth)acrylate, ethyl (meth)acrylate, butyl (meth)acrylate, hexyl (meth)acrylate, tetrahydrofurfuryl (meth)acrylate, 2-hydroxyethyl (meth)acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate and isobornyl (meth)acrylate; silane compounds such as γ-(meth)acryloyloxy propyltrimethoxysilane and γ-(meth)acryloyloxy propyltriethoxysilane; nitrogen-containing compounds such as 2-(N,N-dimethylamino)ethyl (meth)acrylate, N-methylol (meth)acrylamide and diacetone (meth)acrylamide, aromatic bifunctional monomers (crosslinkable monomers): such as 2,2-bis (4-(meth)acryloyloxy phenyl) propane, 2,2-bis (4-(3-(meth)acryloyloxy-2-hydroxypropoxy) phenyl) propane, 2,2-bis (4-(meth)acryloyloxy ethoxyphenyl) propane, 2,2-bis (4-(meth)acryloyloxy diethoxyphenyl) propane, 2,2-bis (4-(meth)acryloyloxy tetraethoxyphenyl) propane, 2,2-bis (4-(meth)acryloyloxy pentaethoxyphenyl) propane, 2,2-bis (4-(meth)acryloyloxy dipropoxyphenyl) propane, 2-(4-(meth)acryloyloxy ethoxyphenyl)-2-(4-(meth)acryloyloxy diethoxyphenyl) propane, 2-(4-(meth)acryloyloxy diethoxyphenyl)-2-(4-(meth)acryloyloxy triethoxyphenyl)propane, 2-(4-(meth)acryloyloxy dipropoxyphenyl)-2-(4-(meth)acryloyloxy triethoxyphenyl)propane, 2,2-bis(4-(meth)acryloyloxy dipropoxyphenyl)propane and 2,2-bis(4-(meth)acryloyloxy isopropoxyphenyl) propane, aliphatic bifunctional monomers (crosslinkable monomers): such as 2-hydroxy-3-acryloyloxypropyl methacrylate, hydroxypivalic acid neopentylglycol di(meth)acrylate, ethyleneglycol di(meth)acrylate, diethyleneglycol di(meth)acrylate, triethyleneglycol di(meth)acrylate, butyleneglycol di(meth)acrylate, polyethyleneglycol di(meth)acrylate, neopentylglycol di(meth)acrylate, propyleneglycol di(meth)acrylate, 1,3-butanediol di(meth)acrylate, 1,4-butanediol di(meth)acrylate, 1,6-hexanediol di(meth)acrylate, and glycerin di(meth)acrylate, trifunctional monomers (crosslinkable monomers): such as trimethylolpropane tri(meth)acrylate, trimethylolethane tri(meth)acrylate, trimethylolmethane tri(meth)acrylate and pentaerythritol tri(meth)acrylate, tetrafunctional monomers (crosslinkable monomers): such as pentaerythritol tetra(meth)acrylate and ditrimethylolporpane tetra (meth)acrylate.

Examples of urethane-based polymerizable monomers include di(meth)acrylates having a biofunctionality, trifunctionality or more-functionality and urethane linkage, which are derived from an adduct of a polymerizable monomer having a hydroxy group such as 2-hydroxyethyl(meth)acrylate, 2-hydroxypropyl (meth)acrylate and 3-chloro-2-hydroxypropyl(meth)acrylate, and a diisocyanate compound such as methylcyclohexane diisocyanate, methylene bis(4-cyclohexyl isocyanate), hexamethylene diisocyanate, trimethyl hexamethylene diisocyanate, isophorone diisocyanate, diisocyanate methylmethylbenzene and 4,4-diphenylmethane diisocyanate.

In addition to the aforementioned (meth)acrylate-based polymerizable monomers, other polymerizable monomer, for example, a monomer, an oligomer or a polymer having at least one polymerizable group in the molecule may be used for the polymerizable monomer in accordance with purpose. The polymerizable monomer other than the (meth)acrylate-based polymerizable monomer may have a substituent such as an acidic group and a fluoro group in the molecule. In the present invention, the polymerizable monomer may be a single component, or may be a mixture of a plurality of polymerizable monomers. If the viscosity of the polymerizable monomer at room temperature is extremely high, or if the polymerizable monomer is solid, this polymerizable monomer is preferably combined with a polymerizable monomer with low viscosity to be used as a mixture of the polymerizable monomers. The above combination is not limited to a combination of two kinds, and may be a mixture of three or more kinds.

The polymerizable monomer may include only monofunctional polymerizable monomers, and may additionally include polyfunctional polymerizable monomers. A preferred polymerizable monomers may include an aromatic compounds of a bifunctional polymerizable monomer and an aliphatic compounds of a bifunctional polymerizable monomer. More preferably, the polymerizable monomers may include 2,2-bis(4-(3-methacryloyloxy-2-hydroxypropoxy)phenyl)propane (Bis-GMA) and triethylene glycol dimethacrylate (TEGDMA).

The polymerizable monomer may include a polymerizable monomer containing an acid group such as a phosphoric acid group, a carboxylic acid group, a phosphonic acid, a sulfonic acid group or the like in the molecule as a part of the polymerizable monomer. The polymerizable monomer may include a polymerizable monomer containing a sulfur atom in the molecule.

It is preferable that the content of the polymerizable monomer containing an acid group such as a phosphoric acid group, a carboxylic acid group, a phosphonic acid, a sulfonic acid group or the like in the molecule is preferably 0.5 to 20 wt. % based on 100% of the polymerizable monomer.

Examples of the polymerizable monomers containing a carboxylic acid group include (meth)acrylic acid, 1,4-di(meth)acryloyloxyethyl pyromellitic acid, 6-(meth)acryloyloxy naphtalene-1,2,6-tricarboxylic acid, N-(meth)acryroyl-p-aminobenzoic acid, N-(meth)acryroyl-5-aminosalicylic acid, 4-(meth)acryroyloxyethyl trimellic acid and anhydride thereof, 4-(meth)acryroyloxybutyl trimellic acid and anhydride thereof, 2-(meth)acryroyloxy benzoic acid, β-(meth)acryroyloxyethyl hydrogen succinate, β-(meth)acryroyloxyethyl hydrogen maleate, 11-(meth)acryloyloxy-1,1-undecane dicarboxylic acid and p-vinylbenzoic acid. Examples of the polymerizable monomers containing a phosphate group include 2-(meth)acryloyloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl) hydrogen phosphate and 2-(meth)acryloyloxyethylphenyl hydrogen phosphate. Examples of the polymerizable monomers containing a sulfonic group include 2-(meth)acrylamide-2-methylpropane sulfonic acid, 4-(meth)acryloyloxy benzene sulfonic acid and 3-(meth)acryloyloxypropanesulfonic acid. Examples of the polymerizable monomers containing sulfur atom include (meth)acrylate having a triazinethiol group, (meth)acrylate having a mercapto group, (meth)acrylate having a polysulfide group, (meth)acrylate having a thiophosphate group, (meth)acrylate having a disulfide cyclic group, (meth)acrylate having a mercaptodithiazole group, (meth)acrylate having a thiouracil group and (meth)acrylate having a thiirane group. These polymerizable monomers may be used alone or in mixture of two or more kinds.

The filler is not specifically limited, and a filler known in the art such as an inorganic filler and/or an organic filler and/or an organic-inorganic composite filler, for example, may be used without restriction. The grain shape of the filler may be any shape such as a sphere, a massive, a needle, a plate, a fracture, a scale, but is not specifically limited. For obtaining a greater stability, the filler preferably has a sphere shape. The degree of circularity of the filler ranges from 0.7 to 1.0, preferably from 0.9 to 1.0, and more preferably from 0.95 to 1.00. The degrees of circularity are determined by taking an image of the particles with a light microscope or a scanning electron microscope (SEM) and analyzing the image with an image analyzer. The number of fillers to be analyzed per sample may be 50 or more. The degrees of circularity are determined based on boundary lengths and area of the fillers. The degree of circularity $e=(4*\Pi*S)/(L^2)$ is calculated with boundary lengths (L) and area (S) of the fillers, which are obtained by analyzing the image.

Specific examples of the inorganic filler include quartz, amorphous silica, aluminum silicate, aluminum oxide, titanium oxide, zirconium oxide, various types of glass (including glass obtained by a melting method, synthetic glass obtained by a sol-gel method, and a glass generated by a gas phase reaction), calcium carbonate, talc, kaoline, clay, mica, aluminum sulfate, calcium sulfate, barium sulfate, calcium phosphate, hydroxyapatite, silicon nitride, aluminum nitride, titanium nitride, silicon carbide, boron carbide, calcium hydroxide, strontium hydroxide, and zeolite. Among these, aluminosilicate glass, borosilicate, aluminoborate and boroaluminosilicate glass containing a heavy metal such as sodium, strontium, barium and lanthanum and/or fluorine are preferable. The average grain size of the inorganic filler is not specifically limited, and is preferably in the range of 0.5 to 10 μm, more preferably in the range of 0.7 to 5 μm.

Ultrafine particle inorganic fillers such as aerosil generated by a gas phase method or particles of silica-zirconia oxide generated from a solution in a sol-gel reaction may also be used. Cohesive inorganic fillers obtained by agglomerating such ultrafine particles may also be used. Cohesive inorganic fillers are crushing during kneading. Crushed inorganic fillers having 1 nm to 300 nm particle diameters are classified as an ultrafine particulate inorganic filler, and crushed inorganic fillers not having 1 nm to 300 nm particle diameter are classified as an inorganic filler.

The ultrafine particulate inorganic filler is preferably, without any limitation, colloidal silica (trade names: Aerosil R972, Aerosil 200, Aerosil 380, Aerosil 50 (Nippon Aerosil Co., Ltd. 5-50 nm)).

The organic filler can be obtained by polymerizing a monomer having a polymerizable group, and the type of the organic filler is not specifically limited. Specific examples of the organic filler include unsaturated aromatics such as polymethyl methacrylate, styrene, α-methylstyrene, halogenated styrene and divinylbenzene; unsaturated esters such as vinyl acetate and vinyl propionate; unsaturated nitriles such as acrylonitrile; and substances obtained by (co)polymerizing a single or a plurality of monomers having a polymerizable group such as butadiene and isoprene. Substances obtained by polymerizing the monomers having a polymerizable group discussed earlier known in the dental field are particularly preferable. The method of preparing the organic filler is not specifically limited, and may be any method in which the monomers having a polymerizable group is subjected to an emulsion polymerization, a suspension polymerization, a dispersion polymerization, or the like, and may be a method in which a polymer bulk generated in advance is pulverized.

The organic-inorganic composite fillers in which inorganic particles are contained in an organic polymer may also be used. The inorganic particles to be contained in the organic polymer are not specifically limited, and those known in the art may be used. Examples of the inorganic particles include particles of the inorganic fillers discussed above. The method of preparing the organic-inorganic composite filler is also not specifically limited, and any method may be used. Examples of the method include a method in which the surfaces of the inorganic particles are microencapsulated or grafted with the organic substance, a method in which the inorganic particles are subjected to a radical polymerization after a polymerizable functional group or a polymerization initiating group is introduced into the surfaces of the inorganic particles, and a method in which a polymer bulk containing inorganic particles generated in advance is pulverized.

Preferably, the average particle diameter of the organic filler and the organic-inorganic composite filler is in a range from 1 to 100 μm. More preferably, the average particle diameter thereof is in a range from 3 to 50 μm and, yet more preferably, is in a range from 5 to 30 μm. The inorganic, organic, and organic-inorganic composite fillers may be used singly or in combination of several kinds thereof.

The filler, such as the inorganic, organic, or organic-inorganic composite filler, may be used after treating the surfaces of the particles of the filler by a method known in the art. For example, the surface treatment may be performed using a surfactant, a fatty acid, an organic acid, an inorganic acid, a silane coupling agent, a titanate coupling agent, polysiloxane, or the like. These surface treatment methods are preferable because the wettability between the resin component and the surface of the filler is improved and the composite material is imparted with superior properties. The surface treatment method may be selected as appropriate according to the required properties. The surface of the filler may be subjected, without restriction, to a surface treatment which uses a special surface treatment agent and/or a special surface treatment method for the purpose of increasing the functionality of the filler.

It is preferable that the content of the filler is 1 to 20 part by weight based on 100 part by weight of the polymerizable monomer.

A known radical generator may be used as a polymerization catalyst. The polymerization catalysts are generally classified into chemical polymerization initiators that initiate polymerization by mixing upon use and photoinitiators that initiate polymerization by light irradiation.

Among such polymerization catalysts, examples of chemical polymerization initiators include redox type polymerization initiator systems comprising an organic peroxide/an amine compound or an organic peroxide/an amine compound/a sulfinic acid salt, or an organic peroxide/an amine compound/a borate compound, and organometal type initiator systems that initiate polymerization by reacting with oxygen or water.

Examples of the aforementioned organic peroxide include benzoylperoxide, parachlorobenzoylperoxide, 2,4-dichlorobenzoyl peroxide, acetyl peroxide, lauroyl peroxide, tertiary-butyl peroxide, cumene hydroperoxide, 2,5-dihydroperoxy-2,5-dimethylhexane, methyl ethyl ketone peroxide, and tertiary-butyl peroxide benzoate.

Examples of the aforementioned amine compound include a secondary or tertiary amine in which an amine group is bound to an aryl group, and particular examples thereof are p-N,N'-dimethyltoluidine, N,N'-dimethylaniline, N'-β-hydroxyethyl-aniline, N,N'-di (β-hydroxyethyl)-aniline, p-N,N'-di (β-hydroxyethyl)-toluidine, N-methyl-aniline, and p-N-methyl-toluidine.

Examples of the aforementioned sulfuric acid salt include sodium benzenesulfinate, lithium benzenesulfinate and sodium p-toluenesulfinate.

Examples of the aforementioned borate compound include a sodium salt, a lithium salt, a potassium salt, a magnesium salt, a tetrabutyl ammonium salt and a tetramethyl ammonium salt of trialkylphenylboron and trialkyl (p-fluorophenyl)boron (wherein the alkyl group is n-butyl group, n-octyl group, n-dodecyl group or the like).

Examples of the aforementioned organometal type polymerizable initiator include organic boron compounds such as triphenylborane, tributylborane and a partial oxide of tributylborane.

The photoinitiator as the polymerization catalyst may be a photosensitizer. The photosensitizer may be used alone or in combination with a photopolymerization promotor. Examples of the aforementioned photosensitizers include α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis(2,6-dimethoxybenzoyl)-2,4,4-trimethylpentylphosphineoxide; α-aminoacetophenones such as 2-benzyl-dimethylamino-1-(4-morpholinophenyl)-butanone-1 and 2-benzyl-diethyl-amino-1-(4-morpholinophenyl)propanone-1; ketals such as benzyldimethylketal, benzyldiethylketal and benzyl(2-methoxyethylketal); titanocenes such as bis (cyclopentadienyl)-bis[2,6-difluoro-3-(1-pyrolyl) phenyl]titanium, bis(cyclopentadienyl)-bis(pentanefluorophenyl)titanium and bis (cyclopentadienyl)-bis(2,3,5,6-tetrafluoro-4-disiloxyphenyl)-titanium.

Examples of the aforementioned photopolymerization promotors include tertiary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylamino benzaldehyde, p-dimethylaminoacetophenone, p-dimethylamino benzoic acid, p-dimethylamino benzoic acid ethyl ester, p-demtethylamino benzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamine N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

These polymerization catalysts may be used alone or as a mixture of two or more thereof. In addition, these polymerization catalysts may be used in combination irrespective of the polymerization form and the kind of polymerization catalysts. The amount of a polymerization catalysts to be added may be appropriately determined depending upon the use. In general, the amount may be selected from a range of 0.1-10 parts by weight based on a polymerizable monomer.

Preferable photopolymerization initiator is a combination of an α-diketone and a tertiary amine and more preferable photopolymerization initiator is a combination of camphorquinone with an aromatic amine having an amino group directly bound to the benzene ring such as ethyl p-N,N-dimethylaminobenzoate or with an aliphatic amine having a double bond in the molecule such as N,N-dimethylaminoethyl methacrylate.

EXAMPLES

Hereinafter, the present invention is described by way of Examples in more detail, and specifically, but the present invention is not limited to these Examples.

[Preparation of Sample]

Dental primer: P1 to P9, Adhesive material: B, and Resin cement: RC were prepared in accordance with an ordinary method by using following component at the formulation ratio shown in Table 1.

(Dental Primer: P1 to P9)
<Organic Solvent>: Anhydrous ethanol, Aceton
<Silane coupling agent>: Methyltrichlorosilane, γ-methacryloyloxypropyltrimethoxysilane
<Acid anhydride>: Citric anhydride, Maleic anhydride, Pyrophosphoric acid
<Strongly acidic compound>: Phosphoric acid
(Adhesive Material: B)
<Polymerizable monomer>: 2-hydroxyethyl (meth)acrylate (2HEMA), 2-hydroxy-3-acryloyloxypropyl methacrylate (2HPA), 2,2-bis(4-(3-methacryloyloxy-2-hydroxypropoxy) phenyl)propane (Bis-GMA), 4-(meth)acryoyloxybuthyl trimellic anhydride (4MABT)
<Polymerization catalyst (photo polymerization initiator)>: Camphor quinone and ethyl p-N,N-dimethylaminobenzoate (Resin Cement: RC)
<Polymerizable monomer>: 2-hydroxyethyl (meth)acrylate (2HEMA), 2-hydroxy-3-acryloyloxypropyl methacrylate (2HPA), 2,2-bis(4-(3-methacryloyloxy-2-hydroxypropoxy) phenyl)propane (Bis-GMA), 4-(meth)acryroyloxybuthyl trimellic anhydride (4MABT)
<Polymerization catalyst (chemical polymerization initiator)>: Benzoylperoxide (BPO) and ethyl p-N,N-dimethylaminobenzoate

[Zirconia Material]
(Preparation of Adherend and Adhesive Body)

Zirconia adherend and Zirconia adhesive body were prepared by cutting and machining the zirconia material "SHOFU DISK ZR-SS LUCENT" (manufactured by Shofu Inc.) using CAD/CAM system and then sintering in accordance with the instruction. The Zirconia adherend (Large) was in a columnar shape formed to have a dimension of 2 cm (diameter) by 1 cm (thickness). The Zirconia adherend (Small) was in a columnar shape formed to have a dimension of 0.5 cm (diameter) by 1 cm (thickness).

(Preparation of Adhesive Test Specimen)

The Zirconia adherend (Large) and the Zirconia adherend (Small) were sandblasted with alumina having an average particle size of about 50 μm (with 0.2 MPa, for 1 second), then were washed with water and dried, and were applied with one of the dental primer: P1 to P8 and dried. Thereafter, Zirconia adherend (Small) were applied with mixed resin cement (RC), and were pressure contacted to the Zirconia adherend (Large). The excess cement was removed. Subsequently, the pressure contacted Zirconia adherend (Large) and the Zirconia adherend (Small) were left for 15 minutes for curing to prepare adhesion test specimen (the number of test specimen N=5).

[Porcelain]
(Preparation of Adherend and Adhesive body)

Porcelain adherend and Porcelain adhesive body were prepared by building-up and sintering "VINTAGE LD" (manufactured by Shofu Inc.) in accordance with the instruction. The Porcelain adherend (Large) was in a columnar shape formed to have a dimension of 2 cm (diameter) by 1 cm (thickness). The Porcelain adherend (Small) was in a columnar shape formed to have a dimension of 0.5 cm (diameter) by 1 cm (thickness).

(Preparation of Adhesion Test Specimen)

The Porcelain adherend (Large) and the Porcelain adherend (Small) were sandblasted with alumina having an average particle size of about 50 μm (with 0.2 MPa, for 1 second), then were washed with water and dried, and were applied with one of the dental primer: P1 to P8 and dried. Thereafter, Porcelain adherend (Small) were applied with mixed resin cement (RC), and were pressure contacted to the Porcelain adherend (Large). The excess cement was removed. Subsequently, the pressure contacted Porcelain adherend (Large) and the Porcelain adherend (Small) were left for 15 minutes for curing to prepare adhesion test specimen (the number of test specimen N=5).

[Composite]
(Preparation of Adherend)

Composite resin adherend was prepared by cutting and machining the resin disk material "SHOFU DISK HC" (manufactured by Shofu Inc.) using CAD/CAM system. The Composite resin adherend was in a columnar shape formed to have a dimension of 2 cm (diameter) by 1 cm (thickness).

(Preparation of Adhesion Test Specimen)

The Composite resin adherend was applied with one of the dental primer: P1 to P8 and dried. Thereafter, Adhesive (B) was applied, and light irradiation was performed for 30 seconds by Griplight 2 (manufactured by Shofu Inc.). The adhesion surface was defined by using jig having a diameter of 0.5 mm, then was filled with composite resin (LITE FIL 2: manufactured by Shofu Inc.). The composite resin was cured by irradiating light for 30 seconds by Griplight 2 (manufactured by Shofu Inc.) to prepare adhesion test specimen (the number of test specimen N=5).

[Adhesion Test Method]
(Initial Adhesion Test)

Adhesion test specimen was immersed in 37° C. g of water for 24 hours. Thereafter, adhesion test was performed.

(Durability Adhesion Test)

Adhesion test specimen was immersed in 37° C. g of water for 24 hours. After immersion, 10000 times of thermal cycle (5° C.<-->50° C., immersion in each temperature for 1 minute) was applied. Thereafter, adhesion test was performed.

(Shelf Life Test)

After preparing the dental primer, 5 cc of the dental primer was collected into an airtight container. The airtight container was preserved for 1 year at a dark cold place of 23° C., and thereafter the Initial adhesion test and Durability adhesion test were performed.

Adhesion test was performed at 23° C. under the atmospheric pressure.

TABLE 1

| Dental primer (g %) | | P1 | P2 | P3 | P4 | P5 | P6 | P7 | P8 | P9 |
|---|---|---|---|---|---|---|---|---|---|---|
| Organic solvent | Anhydrous ethanol | 95 | 95 | 97 | | 77 | 99.5 | 95 | 96 | 95 |
| | Aceton | | | | 95 | | | | | |
| Silane coupling agent | Methyltrichlorosilane | | 4 | | | | | | | |
| | γ-methacryloyloxypropyl trimethoxysilane | 4 | | 2.5 | 2 | 13 | 0.42 | 4 | 4 | 4 |
| Acid anhydride | Citric anhydride | | | | 3 | 10 | 0.08 | | | |
| | Maleic anhydride | 1 | 1 | 0.5 | | | | | | |
| | Pyrophosphoric acid | | | | | | | | 1 | |
| Strongly acidic compound | Phosphoric acid | | | | | | | | | 1 |

| | | Adhesive: B | Resin cement: RC (g %) | |
|---|---|---|---|---|
| | | (g %) | First Paste | Second paste |
| Polymerizable monomer | 2HEMA | 10 | 5 | 5 |
| | 2HPA | 80 | 40 | 40 |
| | Bis-GMA | 2 | 1 | 1 |
| | 4MABT | 5 | 2.5 | 2.5 |

TABLE 1-continued

| | | | |
|---|---|---|---|
| Filler | silane treated glass filler (average particle diameter: 3μ) | 1 | 1 |
| | Aerosil (R972) | 0.1 | 0.1 |
| Photo polymerization initiator | Camphor quinone | 2 | |
| | ethyl p-N,N-dimethylaminobenzoate | 1 | |
| Chemical polymerization initiator | Benzoylperoxide (BPO) | 0.3 | |
| | ethyl p-N,N-dimethylaminobenzoate | | 0.5 |

| Composite resin (CR) |
|---|
| LITE FIL 2 (manufactured by Shofu Inc) |

TABLE 2

| Sample preparation | | Example 1 | Example 2 | Example 3 | Example 4 | Example 5 | Example 6 |
|---|---|---|---|---|---|---|---|
| | Dental primer | P1 | P2 | P3 | P4 | P5 | P6 |
| | Adhesive: B, Resin cement: RC | RC | RC | RC | RC | RC | RC |
| Type of adherend | Zirconia adherend (Large) | ○ | ○ | ○ | ○ | ○ | ○ |
| | Composite resin adherend | | | | | | |
| | Porcelain adherend (Large) | | | | | | |
| Type of adhesive body | Zirconia adherend (Small) | ○ | ○ | ○ | ○ | ○ | ○ |
| | Composite resin | | | | | | |
| | Porcelain adherend (Small) | | | | | | |

| Test Result | | Example 1 | Example 2 | Example 3 | Example 4 | Example 5 | Example 6 |
|---|---|---|---|---|---|---|---|
| Without Shelf life test | Initial adhesion (MP) | 15.5 | 15.2 | 15.3 | 14.8 | 11.5 | 12.0 |
| | Thermal (MP) | 15.4 | 15.1 | 15.2 | 14.4 | 10.2 | 11.5 |
| With Shelf life test | Initial adhesion (MP) | 15.3 | 15.0 | 15.2 | 14.8 | 10.9 | 11.8 |
| | Thermal (MP) | 15.2 | 14.8 | 15.0 | 14.5 | 9.8 | 10.5 |

| Sample preparation | | Example 7 | Example 8 | Example 9 | Example 10 | Example 11 | Example 12 |
|---|---|---|---|---|---|---|---|
| | Dental primer | P1 | P2 | P3 | P4 | P5 | P6 |
| | Adhesive: B Resin cement: RC | B | B | B | B | B | B |
| Type of adherend | Zirconia adherend (Large) | | | | | | |
| | Composite resin adherend | ○ | ○ | ○ | ○ | ○ | ○ |
| | Porcelain adherend (Large) | | | | | | |
| Type of adhesive body | Zirconia adherend (Small) | | | | | | |
| | Composite resin | ○ | ○ | ○ | ○ | ○ | ○ |
| | Porcelain adherend (Small) | | | | | | |

| Test Result | | Example 7 | Example 8 | Example 9 | Example 10 | Example 11 | Example 12 |
|---|---|---|---|---|---|---|---|
| Without Shelf life test | Initial adhesion (MP) | 14.9 | 14.6 | 14.7 | 13.5 | 11.8 | 11.9 |
| | Thermal (MP) | 13.5 | 14.2 | 14.5 | 13.0 | 11.5 | 11.7 |
| With Shelf life test | Initial adhesion (MP) | 14.6 | 14.3 | 14.6 | 13.2 | 10.2 | 10.2 |
| | Thermal (MP) | 14.5 | 14.0 | 14.3 | 13.0 | 9.2 | 9.3 |

| Sample preparation | | Example 13 | Example 14 | Example 15 | Example 16 | Example 17 | Example 18 | Example 19 | Example 20 | Example 21 |
|---|---|---|---|---|---|---|---|---|---|---|
| | Dental primer | P1 | P2 | P3 | P4 | P5 | P6 | P7 | P7 | P7 |
| | Adhesive: B, Resin cement: RC | RC | RC | RC | RC | RC | RC | RC | RC | RC |
| Type of adherend | Zirconia adherend (Large) | | | | | | | ○ | | |
| | Composite resin adherend | | | | | | | | ○ | |
| | Porcelain adherend (Large) | ○ | ○ | ○ | ○ | ○ | ○ | | | ○ |
| Type of adhesive body | Zirconia adherend (Small) | | | | | | | ○ | | |
| | Composite resin | | | | | | | | ○ | |
| | Porcelain adherend (Small) | ○ | ○ | ○ | ○ | ○ | ○ | | | ○ |

| Test Result | | Example 13 | Example 14 | Example 15 | Example 16 | Example 17 | Example 18 | Example 19 | Example 20 | Example 21 |
|---|---|---|---|---|---|---|---|---|---|---|
| Without Shelf life test | Initial adhesion (MP) | 13.4 | 13.4 | 13.6 | 12.5 | 9.9 | 9.7 | 15.3 | 14.5 | 12.6 |
| | Thermal (MP) | 13.2 | 13.3 | 13.2 | 12.1 | 9.8 | 9.4 | 15.2 | 13.8 | 12.1 |
| With Shelf life test | Initial adhesion (MP) | 11.2 | 12.0 | 12.5 | 10.8 | 9.5 | 9.1 | 11.3 | 9.4 | 7.5 |
| | Thermal (MP) | 10.5 | 11.8 | 11.4 | 10.2 | 9.2 | 8.9 | 10.9 | 8.2 | 7.1 |

TABLE 2-continued

| Sample preparation | | Comparative Example 1 | Comparative Example 2 | Comparative Example 3 | Comparative Example 4 | Comparative Example 5 | Comparative Example 6 |
|---|---|---|---|---|---|---|---|
| | Dental primer | P8 | P8 | P8 | P9 | P9 | P9 |
| | Adhesive: B, Resin cement: RC | RC | B | RC | RC | B | RC |
| Type of adherend | Zirconia adherend (Large) | ○ | | | ○ | | |
| | Composite resin adherend | | ○ | | | ○ | |
| | Porcelain adherend (Large) | | | ○ | | | ○ |
| Type of adhesive body | Zirconia adherend (Small) | ○ | | | ○ | | |
| | Composite resin | | ○ | | | ○ | |
| | Porcelain adherend (Small) | | | ○ | | | ○ |

| Test Result | | Comparative Example Example 1 | Comparative Example 1 | Comparative Example 2 | Comparative Example 3 | Comparative Example 4 | Comparative Example 5 |
|---|---|---|---|---|---|---|---|
| Without Shelf life test | Initial adhesion (MP) | 9.1 | 8.7 | 6.5 | fallen off | fallen off | fallen off |
| | Thermal (MP) | 8.7 | 7.4 | 5.1 | | | |
| With Shelf life test | Initial adhesion (MP) | fallen off | fallen off | fallen off | fallen off | fallen off | fallen off |
| | Thermal (MP) | | | | | | |

Used adherend and adhesive body are indicated by "○"

In examples 1 to 4 (adhesion between zirconia and zirconia using resin cement (RC)), examples 7 to 10 (adhesion of composite resin (CR) to composite resin adherend using adhesive material (B)) and examples 13 to 16 (adhesion between porcelain and porcelain using resin cement (RC)) which use the dental primer of the present invention, although the materials and method of adhesive are different in these examples, it was confirmed that adhesive strength was stable in both of Initial adhesion test and Durability adhesion test regardless of "Shelf life test". In addition, in examples 5 to 6 (adhesion between zirconia and zirconia using resin cement (RC)), examples 11 to 12 (adhesion of composite resin (CR) to composite resin adherend using adhesive material (B)) and examples 17 to 18 (adhesion between porcelain and porcelain using resin cement (RC)) which use the dental primer of the present invention, although these examples are inferior to Examples 1 to 4, 7 to 10, and 13 to 16 in adhesive strength, it was confirmed that the same behavior was exhibited and adhesive strength was stable in both of Initial adhesion test and Durability adhesion test regardless of "Shelf life test".

In examples 19-21 (which are examples using pyrophosphoric acid as the acid anhydride), in comparison with an acid anhydride of a weakly acidic compound, it was confirmed that although adhesive strength was stable in both of Initial adhesion test and Durability adhesion test in "With shelf life test", adhesive strength was decreased in both of Initial adhesion test and Durability adhesion test in "Without shelf life test".

On the other hand, in the Comparative Examples 1-3 which use the dental primer containing no acid anhydride, although the materials and method of adhesive are different in these comparative examples, it was confirmed that adhesive strength was stable in both of Initial adhesion test and Durability adhesion test of "Without shelf life test". However, in "With shelf life test", although it was possible to prepare the adhesion test specimen, it was confirmed that adhesive body had already fallen off at the stage of the Initial adhesion test.

Further, in Comparative Examples 4-6 which use dental primer containing a strongly acidic compound, the silane coupling agent which coexisted in the dental primer composition was hydrolyzed after a preparation. Therefore, although it was possible to prepare the adhesion test specimen, it was confirmed that adhesive body had already fallen off at the stage of the Initial adhesion test regardless of "the shelf life examination".

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present invention can be applied in industries because the present invention relates to a dental primer for modifying surface of a dental restoration.

What is claimed is:

1. A set comprising a dental primer for modifying surface of a dental restoration, and an adhesive material, wherein
   the dental primer comprises an organic solvent, a silane coupling agent and an acid anhydride,
   the acid anhydride is an anhydride of a carboxylic acid, a sulfonic acid, a nitric acid and/or a phosphoric acid,
   the dental primer comprises no polymerizable monomer having an acryloyl group and/or a methacryloyl group, and
   the adhesive material comprises a polymerizable monomer, a polymerization catalyst and a filler.

2. The set according to claim 1, wherein the dental primer comprises 80 to 90% by weight of the organic solvent, 0.1 to 15% by weight of the silane coupling agent, and 0.1 to 5% by weight of the acid anhydride.

3. The set according to claim 1, wherein the dental primer comprises no water.

4. The set according to claim 2, wherein the dental primer comprises no water.

5. A set comprising a dental primer for modifying surface of a dental restoration, and an adhesive material, wherein
- the dental primer comprises an organic solvent, a silane coupling agent and an acid anhydride, and
- the adhesive material comprises a polymerizable monomer, a polymerization catalyst and a filler.

6. The set according to claim 5, wherein the dental primer comprises 80 to 90% by weight of the organic solvent, 0.1 to 15% by weight of the silane coupling agent, and 0.1 to 5% by weight of the acid anhydride.

7. The set according to claim 5, wherein the dental primer comprises no water.

8. The set according to claim 6, wherein the dental primer comprises no water.

* * * * *